United States Patent
McKay et al.

(10) Patent No.: US 11,927,590 B2
(45) Date of Patent: Mar. 12, 2024

(54) METHODS AND SYSTEMS FOR SCREENING THERAPEUTIC COMPOSITIONS FOR TREATING AGE-RELATED MACULAR DEGENERATION

(71) Applicant: ARIZONA BOARD OF REGENTS ON BEHALF OF THE UNIVERSITY OF ARIZONA, Tucson, AZ (US)

(72) Inventors: Brian S. McKay, Tucson, AZ (US); Anna G. Figueroa, Tucson, AZ (US); Nicole R. Congrove, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 237 days.

(21) Appl. No.: 17/345,718

(22) Filed: Jun. 11, 2021

(65) Prior Publication Data
US 2021/0389302 A1    Dec. 16, 2021

Related U.S. Application Data

(60) Provisional application No. 63/037,886, filed on Jun. 11, 2020.

(51) Int. Cl.
*G01N 33/50* (2006.01)

(52) U.S. Cl.
CPC ....... *G01N 33/5058* (2013.01); *G01N 33/502* (2013.01)

(58) Field of Classification Search
CPC ............ G01N 33/5058; G01N 33/502; G01N 33/5044
See application file for complete search history.

(56) References Cited

PUBLICATIONS

Locke et al. "Controlled exosome release from the retinal pigment epithelium in situ" Experimental Eye Research 129 (2014) 1-4.

*Primary Examiner* — Jeffrey H Murray
(74) *Attorney, Agent, or Firm* — NGUYEN TARBET LLC

(57) ABSTRACT

Methods and systems for screening therapeutic compositions for the treatment of age-related macular degeneration (AMD) or for the prevention of progression of AMD, wherein retinal pigment epithelium cells (RPE) are cultured and the level of hypoxia-induced exosome release from the RPE cells is subsequently measured. In the present invention, the level of hypoxia-induced exosome release can be correlated with AMD onset and severity.

13 Claims, 3 Drawing Sheets

METHODS AND SYSTEMS FOR SCREENING THERAPEUTIC COMPOSITIONS FOR TREATING AGE-RELATED MACULAR DEGENERATION

CROSS-REFERENCES TO RELATED APPLICATIONS

This application is a non-provisional and claims benefit of U.S. Provisional Application No. 63/037,886 filed Jun. 11, 2020, the specification(s) of which is/are incorporated herein in their entirety by reference.

STATEMENT REGARDING FEDERALLY SPONSORED RESEARCH OR DEVELOPMENT

This invention was made with government support under Grant No. R01 EY026544, awarded by National Institutes of Health. The government has certain rights in the invention.

BACKGROUND OF THE INVENTION

Field of the Invention

The present invention is directed to therapeutic compositions for treating, preventing progression of, or ameliorating symptoms of age-related macular degeneration (AMD), more particularly to screening compositions for therapeutic potential for treating AMD.

Background Art

Age-related macular degeneration (AMD) is a loss of central vision that occurs in either dry, atrophic or wet, exudative (neovascular) forms. Most people with macular degeneration have the atrophic form. According to data from the American Optometrist Association, AMD is the leading cause of severe vision loss in adults over age 50. While there is no specific treatment for atrophic AMD, studies have shown a potential benefit from vitamin supplements, a healthy diet, cessation of smoking, and perhaps intraocular injections. Wet AMD is frequently treated with intraocular injections to inhibit vascular endothelial growth factor (VEGF) activity. However, this line of treatment is expensive.

BRIEF SUMMARY OF THE INVENTION

It is an objective of the present invention to provide methods that allow for the identification of therapeutic compositions for the treatment of AMD, as specified in the independent claims. Embodiments of the invention are given in the dependent claims. Embodiments of the present invention can be freely combined with each other if they are not mutually exclusive.

In some aspects, the present invention features methods and systems for screening agents or therapeutic compositions (e.g., drugs) for the treatment and/or prevention of age-related macular degeneration (AMD), e.g. prevention of development of AMD, prevention of progression of AMD.

Briefly, retinal pigment epithelium cells (RPE) may be cultured and the level of exosome release from the RPE cells may be measured after incubation in a hypoxic environment with candidate therapeutic compositions. The level of exosome release can be correlated with AMD onset and severity. Thus, if a therapeutic composition can reduce exosome release in these RPE assays, then it may be a good candidate drug for treating AMD, preventing its development or progression, or ameliorating symptoms. While exosomes range from 40-140 nm in diameter, these RPE assays are designed to evaluate the cargo and concentration of all extracellular vesicles.

Inventors surprisingly discovered that massive exosome release in retinal pigment epithelial cells (RPEs) is caused by hypoxia and is related to the development and progression of AMD. The current art has no teachings of using hypoxia to release exosomes from RPE cells. Furthermore, the cargo carried by exosomes may identify the form of AMD in a patient. For example, exosomes from patients with dry AMD contain non-angiogenic biomarkers and can be characterized by reduced or absent pigment epithelial derived factor (PEDF), while exosomes from patients with wet AMD contain more angiogenic and pro-inflammatory biomarkers such as vascular endothelial growth factor (VEGF) or IL-6. Further, agents that block or reduce RPE exosome release (e.g., hypoxia-induced RPE exosome release) are believed to be candidates for treating AMD and/or preventing the development or progression of AMD.

The present invention features a rapid method for screening therapeutic compounds that may be used for treating AMD. Current methods for identifying compounds to treat AMD may take up to several years. There is no treatment for dry AMD because it progresses slowly, thus any double blind clinical trial for treating dry AMD needs to be at least 7-9 years to see a minor effect. Neovascular AMD is faster to see an effect largely because the disease process is faster. Once a patient converts from dry AMD to wet AMD, they need to be treated or they will lose significant vision in a year. The methods described herein may take 30 minutes to 4 hours to screen compounds that may be used to treat AMD. In some aspects, for example, the method may use a screen utilizing exosome release from cultured RPE cells in response to hypoxia, with the hypoxic episode lasting just 30 minutes.

The present invention also describes regulating the G-protein coupled receptor (GPCR) GPR143, which is believed to be a target for regulating exosome release and the development and/or progression of AMD. For example, the present invention describes treating AMD and/or preventing the development or progression of AMD by introducing GPR143 agonists such as but not limited to L-DOPA.

The methods herein to screen and identify drug candidates for AMD are scalable to industry levels. For example, the methods here may be used to screen hundreds or thousands of compounds. Candidates from the screen can be further tested, for example tested using hypoxia and laser induced neovascularization animal models as they are moved towards the clinic, etc.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

Terms

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise.

The term "comprising" means that other elements can also be present in addition to the defined elements presented. The use of "comprising" indicates inclusion rather than limitation. Stated another way, the term "comprising" means "including principally, but not necessary solely". Furthermore, variation of the word "comprising", such as "comprise" and "comprises", have correspondingly the same meanings. In one respect, the technology described herein related to the herein described compositions, methods, and respective component(s) thereof, as essential to the invention, yet open to the inclusion of unspecified elements, essential or not ("comprising").

All embodiments disclosed herein can be combined with other embodiments unless the context clearly dictates otherwise.

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999, *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.), the disclosures of which are incorporated in their entirety herein by reference.

All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of the disclosure, the following explanations of specific terms are provided:

As used herein, the term "disease" or "disorder" or "condition" refers to any alteration in state of the body or of some of the organs, interrupting or disturbing the performance of their functions and/or causing symptoms such as discomfort, dysfunction, distress, or even death to the person afflicted or those in contact with a person. A disease or disorder or condition can also relate to a distemper, ailing, ailment, malady, disorder, sickness, illness, complaint, indisposition or affliction.

As used herein, the terms "treat" or "treatment" or "treating" refers to both therapeutic treatment and prophylactic or preventative measures, wherein the object is to prevent or slow the development of the disease, such as slow down the development of a disorder, or reducing at least one adverse effect or symptom of a condition, disease or disorder, e.g., any disorder characterized by insufficient or undesired organ or tissue function. Treatment is generally "effective" if one or more symptoms or clinical markers are reduced as that term is defined herein. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (e.g., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

A "patient" is a subject afflicted with a disease or disorder. The term "patient" includes human and veterinary subjects.

The terms "administering" and "administration" refer to methods of providing a pharmaceutical composition to a subject. Such methods are well known to those skilled in the art and include, but are not limited to, administering the compositions suitable for oral (including buccal and sublingual), nasal, ocular (including subconjunctival, intravitreal, retrobulbar, intracameral), or parenteral (including intraarterial, subcutaneous and intravenous), or the like.

As described above, the compositions can be administered to a subject in a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semi-permeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, anti-inflammatory agents, anesthetics, and the like.

Pharmaceutical formulations may include sterile aqueous or non-aqueous solutions, suspensions, and emulsions. Examples of non-aqueous solvents are propylene glycol, polyethylene glycol, vegetable oils such as olive oil, fish oils, and injectable organic-esters such as ethyl oleate. Aqueous carriers include water, alcoholic/aqueous solutions, emulsions or suspensions, including saline and buffered media. Additional non-limiting examples include sodium chloride solution, Ringer's dextrose, dextrose and sodium chloride, lactated Ringer's, fixed oils, fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Other pharmaceutical formulations include, but are not limited to, powders or granules, suspensions or solutions in water or non-aqueous media, capsules, sachets, or tablets. Thickeners, flavorings, diluents, emulsifiers, dispersing aids or binders may be desirable.

As used herein, the term "artificially inducing" refers to exposing the cultured RPE cells to an artificial stressor. Non-limiting examples of artificial stressors include a hypoxic environment or starvation.

BRIEF DESCRIPTION OF THE SEVERAL VIEWS OF THE DRAWING(S)

The features and advantages of the present invention will become apparent from a consideration of the following detailed description presented in connection with the accompanying drawings in which.

Figure 4A:
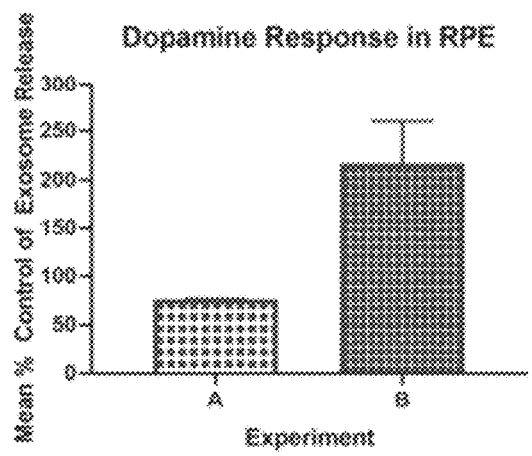
FIG. 4A shows RPE exosome release in response to dopamine. Error bars represent SEM.
Figure 4B:
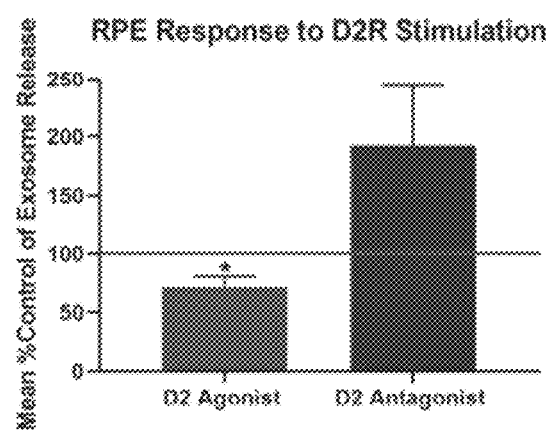

FIG. 4B shows RPE exosome release in response to D2R stimulation. Error bars represent SEM. D2R agonist=bromocriptine; D2R antagonist=raclopride.

Figure 5:
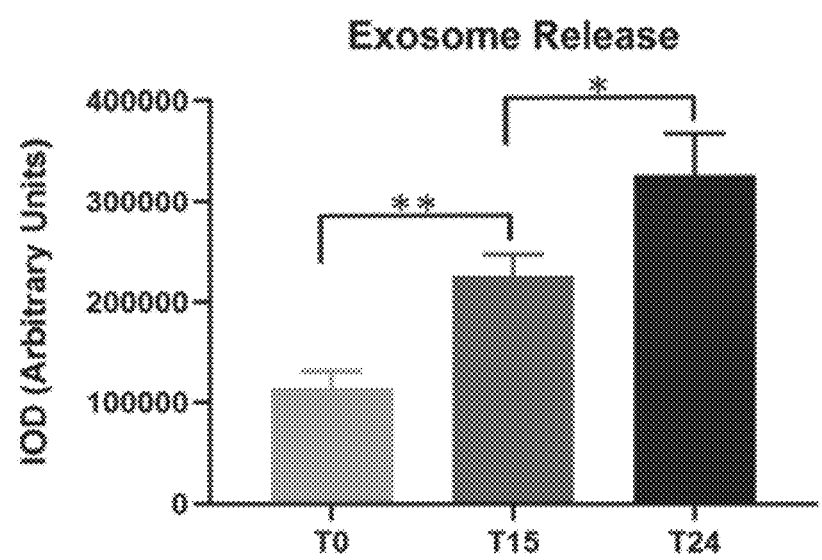

FIG. 5 shows exosome release in response to hypoxia. Exosome release increases the longer RPE undergoes hypoxia. Exosomes can be quantified by unbiased protein staining of SDS-PAGE gels. FIG. 5 shows the composite analysis of 7 experiments in which RPE tissue isolates were treated in triplicate with DMEM 15 hours apart or 24 hours apart. Mean integrated optical density (IOD)+/−SEM, n=21. *P<0.05 **P, 0.01, unpaired t test.

DETAILED DESCRIPTION OF THE INVENTION

Figure 1:
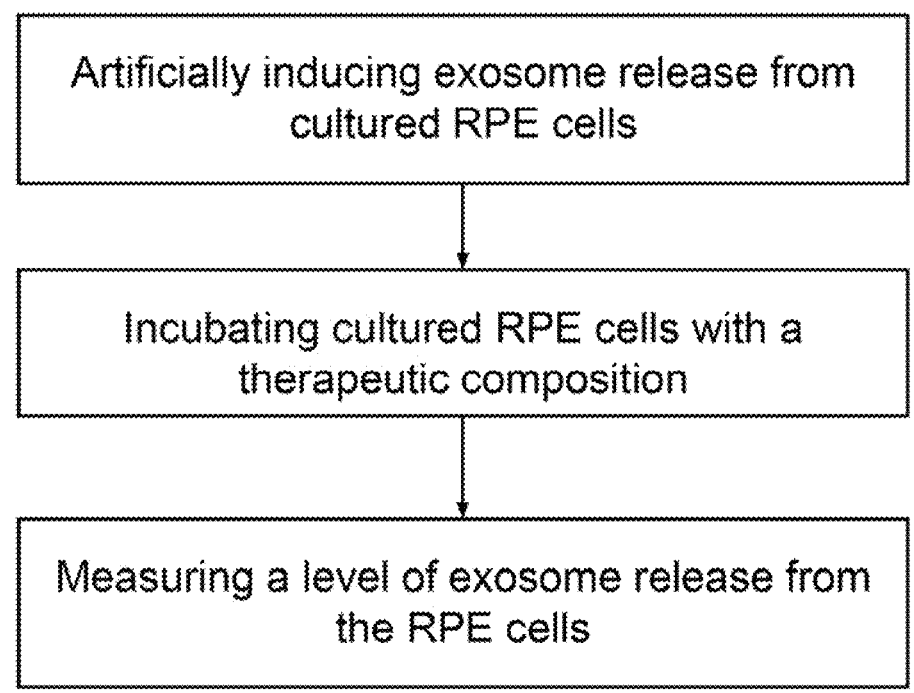
FIG. 1 shows a flow chart of the method of the present invention for identifying a therapeutic composition for treating or preventing progression of age-related macular degeneration (AMD).

Referring now to FIG. 1, the present invention features methods and systems for identifying a therapeutic composition effective for treating a condition caused by increased levels of exosomes released from retinal pigment epithelial (RPE) cells. In some embodiments, the condition caused by increased levels of exosomes released from (RPE) cells is age-related macular degeneration.

In some embodiments, the method comprises artificially inducing exosome release from cultured RPE cells, incubating the cultured RPE cells with a therapeutic composition, and measuring a level of exosome release from the RPE cells. Without wishing to limit the present invention to any theory or mechanism, a therapeutic composition is identified as being effective for treating the condition if the level of exosome release from RPE cells is at least about 10% lower than the predetermined threshold.

In one embodiment, the predetermined threshold is determined by measuring a level of exosome release from a control. In some embodiments, the predetermined threshold is a level of exosome release measured from cultured RPE cells in which exosome release was induced, and then incubated in media without the therapeutic composition. In preferred embodiments, conditions for determining the predetermined threshold are the same as those used in testing the therapeutic composition. Non-limiting examples of conditions include incubation time and the artificial stressor used to induce exosome release. In some embodiments, the therapeutic composition is identified as being effective if the level of exosome release from RPE cells is at least about 10% lower than the predetermined threshold. In some embodiments, the predetermined threshold is a laboratory standard. In other embodiments, the predetermined threshold is an industry standard. In some embodiments, the therapeutic composition is an activator of GPR143.

In some embodiments, exosome release is induced by an artificial stressor. Non-limiting examples of the artificial stressor include a hypoxic environment or starvation. In certain embodiments, the hypoxic oxygen environment is an environment with a concentration of oxygen of about 5%. In certain embodiments, the hypoxic oxygen environment is an environment with a concentration of oxygen of about 10%. In certain embodiments, the hypoxic oxygen environment is an environment with a concentration of oxygen of about 15%. In certain embodiments, the hypoxic oxygen environment is an environment with a concentration of oxygen from 5 to 10%. In certain embodiments, the hypoxic oxygen environment is an environment with a concentration of oxygen from 2 to 15%. In some embodiments, starvation may be induced by incubating the RPE cells with low glucose media. In certain embodiments, the RPE cells are incubated in media with 5 mM glucose to induce starvation. In other embodiments, the RPE cells are incubated in media with 2.5 mM glucose to induce starvation. In some embodiments, the RPE cells are incubated in media with 1.5 mM glucose to induce starvation. In one embodiment, the RPE cells are incubated in media with between 1.5 to 5 mM glucose to induce starvation.

In some embodiments, the method is a high throughput screen. In other embodiments, the RPE cells are cultured in a multi-well plate. Examples of multi-well plates include, but are not limited to, 96 well plates or 384 well plates. In one embodiment, the RPE cells are cultured in a monolayer. In some embodiments, exosome release is induced for a first time period ranging from about 12-24 hours. In another embodiment, the cultured RPE cells are incubated for a second time period ranging from about 15-60 minutes. In other embodiments, the second time period may range from about 30 minutes to about 4 hours. The present invention is not limited to the aforementioned periods of time for incubating the therapeutic composition. In some embodiments, the media may be tyrosine-free, serum-free, exosome-free media (e.g., tyrosine-free, serum-free, exosome-free DMEM).

In further embodiments, the method may comprise collecting a media in which the RPE cells are incubated. In yet another embodiment, the method may further comprise isolating exosomes from the media collected. Without wishing to limit the present invention to any theory or mechanism, the exosomes may indicate which type of AMD a patient has. For example, exosomes from patients with dry AMD contain non-angiogenic biomarkers and are expected to have reduced or absent PEDF, whereas exosomes from patients with wet AMD contain more angiogenic and pro-inflammatory biomarkers, such as VEGF and IL-6.

Exosomes may be quantitated using total exosome protein (e.g., silver stain for SDS-PAGE, UV absorbance, etc.), or exosome counting (e.g., nanoparticle tracking analysis), or other appropriate means. In certain embodiments, measurement of the level of exosome release is performed by measuring an absorbance at 260/280 ($A_{260/280}$) of media in which the RPE cells are cultured. The present invention is not limited to any particular method for measuring levels of exosomes.

The present invention features a composition for treating a condition caused by increased levels of exosomes released from retinal pigment epithelial (RPE) cells. In some embodiments, the composition is identified for treating the condition by inducing exosome release from cultured RPE cells, incubating the cultured RPE cells with a therapeutic composition, and measuring a level of exosome release from the RPE cells. Without wishing to limit the present invention to any theory or mechanism, a therapeutic composition is identified as being effective for treating the condition if the level of exosome release from RPE cells is lower than the predetermined threshold. In some embodiments, the therapeutic composition is identified as being effective for treating the condition if the level of exosome release from RPE cells is at least about 10% lower than the predetermined threshold.

In some embodiments, the present invention features a method of preventing progression of dry age-related macular degeneration (AMD) to wet AMD in a subject in need thereof. The method comprises administering to the subject a therapeutically effective amount of a therapeutic composition identified by the methods described herein. In another embodiment, the present invention features a method for treating AMD in a subject in need thereof. The method comprises administering to the subject a therapeutically effective amount of a therapeutic composition identified by the methods described herein. In preferred embodiments, the therapeutic composition blocks or reduces exosome release in retinal pigment epithelial (RPE) cells.

In some embodiments, the therapeutic compositions are administered in a therapeutically effective amount by any of the accepted modes of administration for agents that serve similar utilities. One of ordinary skill in the art of treating such diseases is typically able, without undue experimentation and in reliance upon personal knowledge and the disclosure of this application, to ascertain a therapeutically effective amount of the therapeutic compositions.

In some embodiments, the therapeutic compositions are administered as pharmaceutical formulations including those suitable for oral (including buccal and sublingual), nasal, ocular (including subconjunctival, intravitreal, retrobulbar, intracameral), or parenteral (including intra-arterial, subcutaneous and intravenous) administration, in a form suitable for administration by inhalation or insufflation, or the like.

In one embodiment, the therapeutic composition may be administered to a patient intranasally, e.g. by using a nasal spray, atomizer, dropper, or syringe. In other embodiments, the therapeutic composition may be administered to a patient orally, e.g. by pill or lozenge form. In yet another embodiment, the therapeutic composition may be administered to a patient in an intravenous dosage. In some embodiments, the therapeutic composition may be administered to a patient ocularly, e.g. by eye drops.

The present invention features methods and systems for screening agents or therapeutic compositions (e.g., drugs) for the treatment and/or prevention of age-related macular degeneration (AMD), e.g. prevention of development of AMD, prevention of progression of AMD.

Retinal pigment epithelium cells (RPE) may be cultured and the level of hypoxia-induced exosome release from the RPE cells is subsequently measured after incubation with candidate therapeutic compositions at different oxygen concentrations (e.g., normal oxygen versus an oxygen level considered to provide a hypoxic environment). For example, monolayers of RPEs (e.g., pigmented RPEs) may be grown. In some embodiments, RPE are left undisturbed at confluence for a period of time, e.g., a minimum of 2-4 months, while maintained in low tyrosine medium. Media may include a tyrosine-free, serum-free, exosome-free media (e.g., tyrosine-free, serum-free, exosome-free DMEM).

A portion of cells may then be placed in a hypoxic environment (e.g., 5% $O_2$ concentration) for 24 hours to induce exosome release, and a portion may be placed in an environment with a normal oxygen concentration. A candidate therapeutic composition may be introduced to the cells for a period of time, e.g., 15 minutes, 30 minutes, 45 minutes, 60 minutes, 90 minutes, 2 hours, 3 hours, 4 hours, or a period of time between 15 minutes to 4 hours, etc. The present invention is not limited to the aforementioned periods of time for incubating the candidate therapeutic composition. Following incubation with the candidate therapeutic composition, the level of exosomes may be measured. In certain embodiments, the level of protein in the media is measured directly, e.g., without purifying any particular proteins, etc. In certain embodiments, the media is collected, exosomes are isolated, and levels of exosomes are measured. Methods of isolating exosomes are well known to one of ordinary skill in the art (e.g., polyethylene glycol precipitation). The present invention is not limited to the aforementioned methods of measuring levels of exosomes.

Exosomes may be quantitated using total exosome protein (e.g., silver stain for SDS-PAGE, UV absorbance, etc.), or exosome counting (e.g., nanoparticle tracking analysis), or other appropriate means. In certain embodiments, total exosome protein is measured using direct 260/280 absorbance. The present invention is not limited to any particular method for measuring levels of exosomes.

The exosome protein levels may be compared between the drug-treated cells and the control cells. Further, the level of exosome release can be correlated with AMD onset and severity. Thus, if a therapeutic composition can reduce exosome release in RPE assays, then it may be a good candidate drug for treating AMD, preventing its development or progression, or ameliorating symptoms.

The methods of the present invention may be carried out using any appropriate cell culture plates, including multi-well plates such as 12-well plates, 48-well plates, 96-well plates, 384-well plates, etc. Thus, the present invention provides for a high-throughput screening method.

Table 1 below illustrates one embodiment of the screening method of the present invention. The present invention is not limited to the methods, assays, conditions, or compositions described herein.

TABLE 1

| Step | Description |
|---|---|
| 1 | Grow monolayers of pigmented RPE |
| 2 | Place cells in hypoxic $O_2$ environment for a period of time to induce exosome release |
| 3 | Add test compound (e.g., drug) to be tested, incubate for a period of time |
| 4 | Collect conditioned media with exosomes |
| 5 | Isolate exosomes by any appropriate method (eg., polyethylene glycol precipitation, exosome isolation kit, etc.) |
| 6 | Measure protein in isolated exosomes (any appropriate method to measure, e.g., direct 260/280 absorbance) |
| 7 | Compare exosome protein amounts between drug treated and control media (or compare exosome protein amounts between drug treated media and a predetermined threshold) |

In certain embodiments, the RPE cells must be pigmented, so the cells may be left undisturbed at confluence for a period of time, e.g., minimum of 2-4 months. Note that tyrosine may cause inactivation of the GPR143 receptor, so the cells may be maintained in low tyrosine medium supplemented with dialyzed FBS. In certain embodiments, before the assay (e.g., 24-hours prior to assay), cells are switched to tyrosine-free, serum-free, exosome-free media so there is no detectable exosome contamination from the medium alone.

In certain embodiments, the hypoxic oxygen environment is an environment with a concentration of oxygen of about 5%. In certain embodiments, the hypoxic oxygen environment is an environment with a concentration of oxygen of about 10%. In certain embodiments, the hypoxic oxygen environment is an environment with a concentration of oxygen of about 15%. In certain embodiments, the hypoxic oxygen environment is an environment with a concentration of oxygen from 2 to 10%. In certain embodiments, the hypoxic oxygen environment is an environment with a concentration of oxygen from 5 to 15%.

In certain embodiments, the RPE cells are not placed in the hypoxic environment for a period of time prior to addition of the test compound or drug, e.g., the test compound is added at the time the cells are placed in the hypoxic oxygen environment.

In certain embodiments, the cells are incubated in a hypoxic $O_2$ environment to induce exosome release for a time period between 30 minutes to 4 hours. In certain embodiments, the cells are incubated in a hypoxic $O_2$ environment to induce exosome release for a time period between 1 to 5 hours. In certain embodiments, the cells are incubated in a hypoxic $O_2$ environment to induce exosome release for a time period between 4 to 10 hours. In certain embodiments, the cells are incubated in a hypoxic $O_2$ environment to induce exosome release for a time period between 5 to 15 hours. In certain embodiments, the cells are incubated in a hypoxic $O_2$ environment to induce exosome release for a time period between 12 to 24 hours. In certain embodiments, the cells are incubated in a hypoxic $O_2$ environment to induce exosome release for a time period between 15 to 24 hours. In certain embodiments, the cells are incubated in a hypoxic $O_2$ environment to induce exosome release for a time period between 20 to 30 hours. The present invention is not limited to the aforementioned time periods.

In certain embodiments, the cells are incubated with the test compound or drug for a time period from 10 to 30 minutes. In certain embodiments, the cells are incubated with the test compound or drug for a time period from 20 to 30 minutes. In certain embodiments, the cells are incubated with the test compound or drug for a time period from 20 to 45 minutes. In certain embodiments, the cells are incubated with the test compound or drug for a time period from 30 to 60 minutes. In certain embodiments, the cells are incubated with the test compound or drug for a time period from 60 to 90 minutes. In certain embodiments, the cells are incubated with the test compound or drug for a time period from 1-3 hours. In certain embodiments, the cells are incubated with the test compound or drug for a time period greater than 3 hours. The present invention is not limited to the aforementioned time periods.

In some embodiments, the present invention features a kit for screening compounds that are effective for treating age-related macular degeneration (AMD). In some embodiments, the kit comprises: at least two containers for culturing and incubating retinal pigment epithelial (RPE) cells, RPE cells, tyrosine-free, serum-free, and exosome-free media, and a set of instructions for identifying a compound that is effective for treating AMD. In further embodiments, the set of instructions comprises: culturing the RPE cells in each container with the media; artificially inducing exosome release from the RPE cells; adding the compound to the RPE cells in one of the containers; incubating the RPE cells in each container; and measuring a level of exosome release from the RPE cells in each container. Without wishing to limit the present invention to any theory or mechanism, if the level of exosome release from the RPE cells in the container with the compound is at least 10% lower than the level of exosome release from the RPE cells in the container without the compound, then the compound is identified as being effective for treating AMD. In some embodiments, the culture dish is a multi-well plate. Non-limiting examples of multi-well plates include 96 well plates and 384 well plates. In other embodiments, the kit further comprises components and instructions for isolating exosomes.

Example

The following example describes the regulation of RPE-exosome release with L-DOPA. The present invention is not limited to the methods or materials described herein.

Exosomes serve as a critical inter-tissue communication and transport system, which may serve a vital role in RPE: retina interaction. Exosomes are small (40-100 nm diameter) extracellular vesicles produced within the multivesicular body (MVB), which is a multipurpose organelle of the endosomal system. The MVB fuses with the plasma membrane and releases the intraluminal vesicles as exosomes in a controlled manner.

Figure 2:
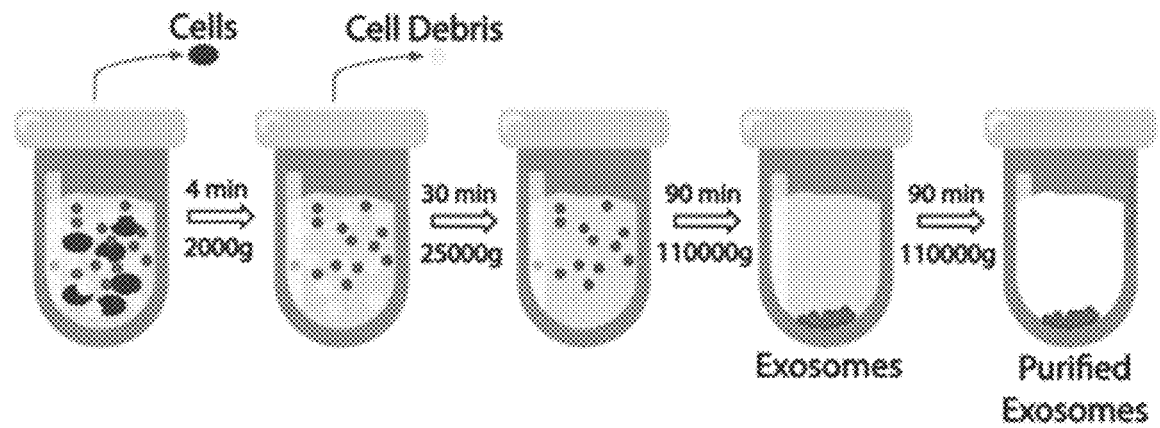
FIG. 2 shows a schematic view of exosome isolation using differential ultracentrifugation. Exosomes can be quantitated using total exosome protein (e.g., silver stain for SDS-PAGE, UV absorbance, etc.), or exosome counting (e.g., nanoparticle tracking analysis), or other appropriate means.

Exosomes released from retinal pigment epithelial (RPE) cells can be isolated. For example, FIG. 2 shows a schematic view of exosome isolation using differential ultracentrifugation. Cells and cell debris are removed and exosomes are then purified. Note the present invention is not limited to this particular method of exosome isolation. In certain embodiments of the present invention, exosomes are not isolated for the measurement of levels of exosomes released from RPE cells.

Figure 3A:
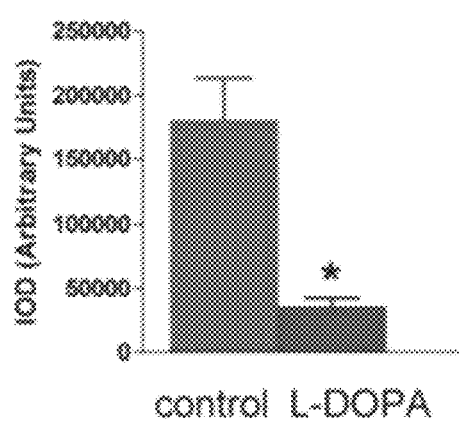
FIG. 3A shows RPE-exosome release in response to L-DOPA.
Figure 3B:
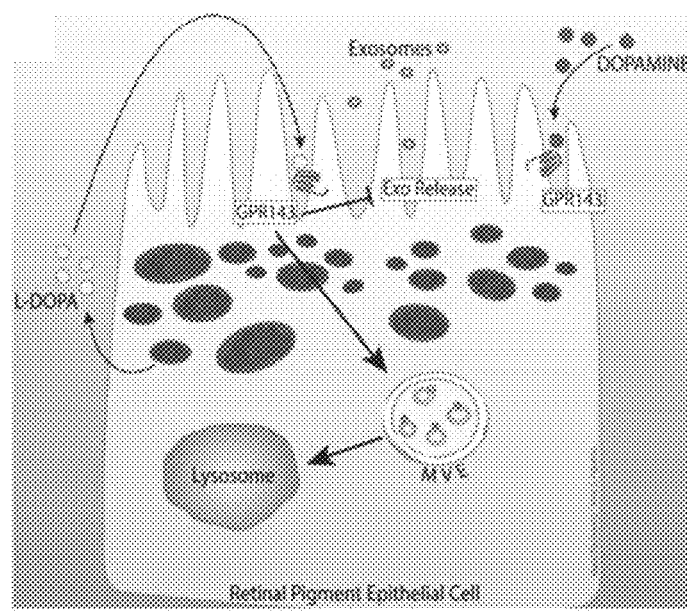
FIG. 3B shows a schematic view of RPE-exosome release in response to L-DOPA.

Referring to FIG. 3A, RPE cells were incubated in either media (e.g., DMEM) or media (e.g., DMEM) plus L-DOPA, showing a significant reduction in exosome release in the L-DOPA-treated RPE cells. FIG. 3B illustrates GPR143 exosome release and its inhibition by L-DOPA.

FIG. 4A and FIG. 4B show RPE exosome release studies in response to 30 minute treatments with 1 µM dopamine (FIG. 4A), 1 nM Dopamine 2 receptor (D2R) agonist (bromocriptine, FIG. 4B), and 1 nM Dopamine 2 receptor (D3R) antagonist (raclopride, FIG. 4B). These studies illustrate that stimulation of the D2R in the RPE reduces the release of exosomes.

FIG. 5 shows an exosome release study in response to hypoxia. RPE tissue isolates were cultured for 15 hours or 24 hours. Exosomes were quantified by unbiased protein staining of SDS-PAGE gels. The results show that exosome release increases the longer RPE undergoes hypoxia.

Embodiments of the present invention can be freely combined with each other if they are not mutually exclusive.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

What is claimed is:

1. A method of identifying a therapeutic composition effective for treating a condition caused by increased levels of exosomes released from retinal pigment epithelial (RPE) cells, said method comprising:
   a. artificially inducing exosome release from cultured RPE cells;
   b. incubating the cultured RPE cells from a) with a therapeutic composition, wherein the cultured RPE cells incubated with the therapeutic composition continue to release exosomes; and
   c. measuring a level of exosomes released from the cultured RPE cells incubated with the therapeutic composition;
   wherein if the level of exosomes released from the cultured RPE cells incubated with the therapeutic composition is lower than a predetermined threshold, then the therapeutic composition is identified as being effective for treating the condition.

2. The method of claim 1, wherein the condition caused by increased levels of exosomes released from RPE cells is age-related macular degeneration (AMD).

3. The method of claim 1, wherein the predetermined threshold is a level of exosomes released measured from cultured RPE cells in which exosome release was artificially induced, and then incubated in media without the therapeutic composition.

4. The method of claim 1, wherein if the level of exosomes released from cultured RPE cells incubated with the therapeutic composition is at least about 10% lower than the predetermined threshold, the therapeutic composition is identified as being effective for treatment.

5. The method of claim 1, wherein media from the cultured RPE cells incubated with the therapeutic composition is collected for measuring the level of exosomes released from the cultured RPE cells.

6. The method of claim 5 further comprising isolating exosomes from the media collected.

7. The method of claim 1, wherein measuring the level of exosomes released from the RPE cells incubated with or without the therapeutic composition, is performed by measuring an absorbance at 260/280 ($A_{260/280}$) of media in which the RPE cells are cultured.

8. The method of claim 1, wherein artificially inducing exosome release comprises artificially inducing the cultured RPE cells with an artificial stressor.

9. The method of claim 8, wherein the artificial stressor is a hypoxic environment or starvation.

10. The method of claim 9, wherein the hypoxic environment is an environment with a concentration of oxygen between about 5-10%.

11. The method of claim 1, wherein exosome release is artificially induced for a first time period ranging from about 12-24 hours.

12. The method of claim 11, wherein the cultured RPE cells are incubated with or without the therapeutic composition for a second time period ranging from about 15-60 minutes.

13. The method of claim 1, wherein the therapeutic composition is an activator of GPR143.

* * * * *